United States Patent
Marotti et al.

(10) Patent No.: US 6,511,813 B1
(45) Date of Patent: Jan. 28, 2003

(54) ELONGATION FACTOR P (EFP) AND ASSAYS AND ANTIMICROBIAL TREATMENTS RELATED TO THE SAME

(75) Inventors: Keith R. Marotti, Kalamazoo, MI (US); Roger A. Poorman, Kalamazoo, MI (US); Peter A. Wells, Kalamazoo, MI (US); Dean L. Shinabarger, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/704,321

(22) Filed: Nov. 2, 2000

Related U.S. Application Data

(62) Division of application No. 09/322,732, filed on May 28, 1999.
(60) Provisional application No. 60/117,473, filed on Jan. 27, 1999.

(51) Int. Cl.[7] ............................................. G01N 33/53
(52) U.S. Cl. ........................... 435/7.1; 435/6; 530/350; 530/300; 536/23.1; 514/2
(58) Field of Search ..................... 435/7.1, 6; 536/23.1; 530/350, 300; 514/2

(56) References Cited

U.S. PATENT DOCUMENTS

| | | | |
|---|---|---|---|
| 3,117,122 A | 1/1964 | Felder et al. | 260/240 |
| 3,141,889 A | 7/1964 | Ebetino | 260/307 |
| 3,149,119 A | 9/1964 | Ebetino | 260/306.8 |
| 3,177,114 A | 4/1965 | Cantor et al. | 167/17 |
| 3,318,878 A | 5/1967 | Dunn | 260/240 |
| 3,322,712 A | 5/1967 | Gardner et al. | 260/29.6 |
| 3,513,238 A | 5/1970 | Kuhn et al. | 424/272 |
| 3,546,241 A | 12/1970 | Hickner et al. | 260/307 |
| 3,598,812 A | 8/1971 | Hoyle et al. | 260/240 |
| 3,598,830 A | 8/1971 | Berkelhammer et al. | 260/302 D |
| 3,632,577 A | 1/1972 | Hoyle et al. | 260/240 A |

(List continued on next page.)

FOREIGN PATENT DOCUMENTS

| | | |
|---|---|---|
| EP | 0 500 868 | 9/1992 |
| EP | 0 610 265 | 8/1994 |
| EP | 0 673 370 | 9/1995 |

OTHER PUBLICATIONS

Glick et al., Eur. J. Biochem., vol. 71, pp. 483–491, 1976.*
Glick et al., Eur. J. Biochem., vol. 97, pp. 23–28, 1979.*
Ohta et al., Nature, vol. 219, pp. 28–243, 1968.*
Mizuno, Biochimica Et Biophysica Acta, vol. 383, No. 2, pp. 207–214, 1975.*
Aoki et al., "Molecular Characterization of the Procaryotic Efp Gene Product Involved in a Peptidyltransferase Reaction," *Biochimie*, 1997, 79, 7–11.
Aoki et al., "Cloning, sequencing and overexpression of the gene for prokaryotic factor EF–P involved in peptide bond synthesis," *Nucl. Acids Res.*, 1991, 19(22), 6215–6220.
Aoki, H., et al., "The gene encoding the elongation factor P protein is essential for viability and is required for protein synthesis," *J. Biological Chem.*, 1997, 272(51), 32254–32259.
Benne et al., "Purification and Characterization of Protein Synthesis Initiation Factors eIF–1, eIF–4D, and eIF–5 from Rabbit Reticulocytes," *J. Biol. Chem.*, 1978, 253(9), 3070–3077.
Benne et al., "The Mechanism of Action of Protein Synthesis Initiation Factors from Rabbit Reticulocytes," *J. Biol. Chem.*, 1978, 253(9), 3078–3087.
Chung, D–G. et al., "Peptidyltransferase: the soluble protein EF–P restores the efficiency of 70S ribosome–catalysed peptide–bond synthesis," in *Ribosomes and Proteins Synthesis, A Practical Approach*, Spedding, G. (ed.), IRL Press at Oxford University, Oxford, NY, 1990, Ch. 4, 69–80.
Ganoza, M.C. et al., "Stimulation of peptidyltransferase reactions by a soluble protein," *Eur. J. Biochem.*, 1985, 146, 287–294.
Lin, A.H. et al., "The Oxazolidinone Eperezolid Binds to the 50S Ribosomal Subunit and Competes with Binding of Chloramphenicol and Lincomycin," *Antimicrobial Agents and Chemotherapy*, 1997, 41(10), 2127–2131.
Moldave, K., "Eukaryotic Protein Synthesis," *Ann. Rev. Biochem.*, 1985, 54, 1109–1149.
Monro et al., "Ribosomal Peptidyltransferase: The Fragment Reaction," *Methods Enzymol.*, 1971, 20, 472–481.
Monro et al., "Ribosome–catalysed Reaction of Puromycin with a Formylmethionine–containing Oligonucleotide," *J. Mol. Biol.*, 1967, 25, 347–350.
Smit–McBride et al., "Sequence Determination and cDNA Cloning of Eukaryotic Initiation Factor 4D, the Hypusine–containing Protein," *J. Biol. Chem.*, 1989, 264(3), 1578–1583.
Swaney, S.M. et al., "The Oxazolidinone Linezolid Inhibits Initation of Protein Synthesis in Bacteria," *Antimicrobial Agents and Chemotherapy*, 1998, 42(12), 3251–3255.

Primary Examiner—Karen Cochrane Carlson
Assistant Examiner—Hope A. Robinson
(74) Attorney, Agent, or Firm—Cozen O'Connor, P.C.

(57) ABSTRACT

Disclosed are novel methods of using elongation factor p (efp) and related constituents of ribosomal complexes which comprise efp, the 50S ribosomal subunit, the 30S ribosomal subunit, the 70S initiation complex, and related proteins, cofactors and enzymes. Methods of identifying compounds which modulate prokaryotic elongation factor p and modify cell function are described. Both in vitro and in vivo methods for identifying compounds which modulate such constituents and affect cell function are described. Such identified compounds, including various antibiotics, which specifically affect cell growth, methods of treating various disorders with such compounds, and antiseptics containing such compounds are described. The present invention is also directed to methods and compounds that modulate prokaryotic elongation factor p.

9 Claims, No Drawings

U.S. PATENT DOCUMENTS

| | | |
|---|---|---|
| 3,674,780 A | 7/1972 | Berkelhammer et al. ............... 260/240 G |
| 3,678,040 A | 7/1972 | Esteve et al. ........... 260/240 A |
| 3,686,170 A | 8/1972 | Hoyle et al. ............ 260/240 A |
| 3,794,665 A | 2/1974 | Berkelhammer et al. ................ 260/306.8 D |
| 3,906,101 A | 9/1975 | Hoyle et al. ................. 424/272 |
| 3,947,465 A | 3/1976 | Coll ....................... 260/307 C |
| 4,000,293 A | 12/1976 | Kaminski et al. ........... 424/272 |
| 4,007,168 A | 2/1977 | Coll ........................ 260/239.1 |
| 4,193,918 A | 3/1980 | Bianchini et al. ........ 260/239.1 |
| 4,243,801 A | 1/1981 | Wright ..................... 536/17 R |
| 4,340,606 A | 7/1982 | Fugitt et al. ................. 424/272 |
| 4,362,866 A | 12/1982 | Igarashi et al. ............ 536/16.8 |
| 4,461,773 A | 7/1984 | Gregory ..................... 424/272 |
| 4,568,649 A | 2/1986 | Beretoglio-Matte ......... 436/534 |
| 4,642,351 A | 2/1987 | Woo et al. .................. 548/317 |
| 4,665,171 A | 5/1987 | Evans et al. ................ 540/364 |
| 4,668,517 A | 5/1987 | Weber et al. ............... 424/469 |
| 4,705,799 A | 11/1987 | Gregory ..................... 514/376 |
| 4,734,495 A | 3/1988 | Evans et al. ................ 540/364 |
| 4,775,752 A | 10/1988 | Evans et al. ................ 540/364 |
| 4,791,207 A | 12/1988 | Salzmann et al. .......... 548/110 |
| 4,801,600 A | 1/1989 | Wang et al. ................ 514/376 |
| 4,870,169 A | 9/1989 | Evans et al. ................ 540/229 |
| 4,877,892 A | 10/1989 | Brittelli ...................... 549/552 |
| 4,921,869 A | 5/1990 | Wang et al. ................ 514/376 |
| 4,948,801 A | 8/1990 | Carlson et al. ............. 514/307 |
| 4,965,268 A | 10/1990 | Wang et al. ................ 514/253 |
| 5,036,092 A | 7/1991 | Wang et al. ................ 514/376 |
| 5,043,443 A | 8/1991 | Carlson et al. ............. 544/112 |
| 5,130,316 A | 7/1992 | Carlson et al. ............. 514/255 |
| 5,164,510 A | 11/1992 | Brickner ..................... 548/231 |
| 5,182,403 A | 1/1993 | Brickner ..................... 548/231 |
| 5,208,329 A | 5/1993 | DiNinno et al. ............. 540/302 |
| 5,220,011 A | 6/1993 | DiNinno et al. ............. 540/302 |
| 5,225,565 A | 7/1993 | Brickner ..................... 548/229 |
| 5,231,188 A | 7/1993 | Brickner ..................... 548/221 |
| 5,247,090 A | 9/1993 | Brickner ...................... 546/89 |
| 5,254,577 A | 10/1993 | Carlson et al. ............. 514/376 |
| 5,523,403 A | 6/1996 | Barbachyn .................. 544/137 |
| 5,529,998 A | 6/1996 | Häbich et al. ........... 514/233.8 |
| 5,532,261 A | 7/1996 | DiNinno et al. ............. 514/210 |
| 5,534,636 A | 7/1996 | Tegeler et al. .............. 548/228 |
| 5,547,950 A | 8/1996 | Hutchinson et al. ........ 514/252 |
| 5,565,571 A | 10/1996 | Barbachyn et al. ......... 546/144 |
| 5,618,949 A | 4/1997 | Ma et al. .................... 548/557 |
| 5,627,181 A | 5/1997 | Riedl et al. .............. 514/236.8 |
| 5,627,197 A | 5/1997 | Gante et al. ................ 514/326 |
| 5,652,238 A | 7/1997 | Brickner et al. ......... 514/235.8 |
| 5,654,428 A | 8/1997 | Barbachyn et al. ......... 544/235 |
| 5,654,435 A | 8/1997 | Barbachyn et al. ........ 546/271.4 |
| 5,668,286 A | 9/1997 | Yamada et al. ............ 546/209 |
| 5,684,023 A | 11/1997 | Riedl et al. ................ 514/337 |
| 5,688,792 A | 11/1997 | Barbachyn ............... 514/235.5 |
| 5,698,574 A | 12/1997 | Riedl et al. ................. 514/376 |
| 5,700,799 A | 12/1997 | Hutchinson et al. ..... 514/235.8 |
| 5,719,154 A | 2/1998 | Tucker et al. ............... 514/252 |
| 5,736,545 A | 4/1998 | Gadwood et al. .......... 514/252 |
| 5,756,732 A | 5/1998 | Barbachyn et al. ......... 544/112 |
| 5,776,937 A | 7/1998 | Gante et al. ................ 514/252 |
| 5,910,504 A | 6/1999 | Hutchinson ................. 514/376 |
| 5,922,707 A | 7/1999 | Thomas et al. .......... 514/230.2 |

\* cited by examiner

SEQUENCE LISTING

```
<160> NUMBER OF SEQ ID NOS: 3

<210> SEQ ID NO 1
<211> LENGTH: 185
<212> TYPE: PRT
<213> ORGANISM: Staphylococcus aureus

<400> SEQUENCE: 1

Met Ile Ser Val Asn Asp Phe Lys Thr Gly Leu Thr Ile Ser Val Asp
1               5                   10                  15

Asn Ala Ile Trp Lys Val Ile Asp Phe Gln His Val Lys Pro Gly Lys
            20                  25                  30

Gly Ser Ala Phe Val Arg Ser Lys Leu Arg Asn Leu Arg Thr Gly Ala
        35                  40                  45

Ile Gln Glu Lys Thr Phe Arg Ala Gly Glu Lys Val Glu Pro Ala Met
    50                  55                  60

Ile Glu Asn Arg Arg Met Gln Tyr Leu Tyr Ala Asp Gly Asp Asn His
65                  70                  75                  80

Val Phe Met Asp Asn Glu Ser Phe Glu Gln Thr Glu Leu Ser Ser Asp
                85                  90                  95

Tyr Leu Lys Glu Glu Leu Asn Tyr Leu Lys Glu Gly Met Glu Val Gln
            100                 105                 110

Ile Gln Thr Tyr Glu Gly Glu Thr Ile Gly Val Glu Leu Pro Lys Thr
        115                 120                 125

Val Glu Leu Thr Val Thr Glu Thr Glu Pro Gly Ile Lys Gly Asp Thr
    130                 135                 140

Ala Thr Gly Ala Thr Lys Ser Ala Thr Val Glu Thr Gly Tyr Thr Leu
145                 150                 155                 160

Asn Val Pro Leu Phe Val Asn Glu Gly Asp Val Leu Ile Ile Asn Thr
                165                 170                 175

Gly Asp Gly Ser Tyr Ile Ser Arg Gly
            180                 185

<210> SEQ ID NO 2
```

```
<211> LENGTH: 188
<212> TYPE: PRT
<213> ORGANISM: Escherichia coli

<400> SEQUENCE: 2

Met Ala Thr Tyr Tyr Ser Asn Asp Phe Arg Ala Gly Leu Lys Ile Met
1               5                   10                  15

Leu Asp Gly Glu Pro Tyr Ala Val Glu Ala Ser Glu Phe Val Lys Pro
            20                  25                  30

Gly Lys Gly Gln Ala Phe Ala Arg Val Lys Leu Arg Arg Leu Leu Thr
            35                  40                  45

Gly Thr Arg Val Glu Lys Thr Phe Lys Ser Thr Asp Ser Ala Glu Gly
        50                  55                  60

Ala Asp Val Val Asp Met Asn Leu Thr Tyr Leu Tyr Asn Asp Gly Glu
65                  70                  75                  80

Phe Trp His Phe Met Asn Asn Glu Thr Phe Glu Gln Leu Ser Ala Asp
                85                  90                  95

Ala Lys Ala Ile Gly Asp Asn Ala Lys Trp Leu Leu Asp Gln Ala Glu
                100                 105                 110

Cys Ile Val Thr Leu Trp Asn Gly Gln Pro Ile Ser Val Thr Pro Pro
            115                 120                 125

Asn Phe Val Glu Leu Glu Ile Val Asp Thr Asp Pro Gly Leu Lys Gly
        130                 135                 140

Asp Thr Ala Gly Thr Gly Gly Lys Pro Ala Thr Leu Ser Thr Gly Ala
145                 150                 155                 160

Val Val Lys Val Pro Leu Phe Val Gln Ile Gly Glu Val Ile Lys Val
                165                 170                 175

Asp Thr Arg Ser Gly Glu Tyr Val Ser Arg Val Lys
            180                 185

<210> SEQ ID NO 3
<211> LENGTH: 29
<212> TYPE: DNA
<213> ORGANISM: Artificial Sequence
<220> FEATURE:
<223> OTHER INFORMATION: Synthetic oligoribonucleotide

<400> SEQUENCE: 3
gggaauucgg agguuuaaaa auggguaaa                                29
```

ELONGATION FACTOR P (EFP) AND ASSAYS AND ANTIMICROBIAL TREATMENTS RELATED TO THE SAME

CROSS-REFERENCE TO RELATED APPLICATIONS

The present application claims priority to provisional U.S. application Ser. No. 60/117,473 filed Jan. 27, 1999, which is incorporated herein by reference in its entirety and is a divisional of U.S. application Ser. No. 09/322,732, filed May 28, 1999.

FIELD OF THE INVENTION

The present invention is directed, in part, to methods of using elongation factor p (efp) and related constituents of ribosomal complexes which comprise efp, the 50S ribosomal subunit, the 30S ribosomal subunit, the 70S ribosome, and related proteins, cofactors and enzymes to identify compounds that modulate prokaryotic cell function. Antibiotic compounds affecting such cell functions and methods of using those compounds to treat microbial infections in mammals are also described.

BACKGROUND OF THE INVENTION

An important catalytic function of ribosomes is the synthesis of peptide bonds. Various studies have suggested that the 70S ribosome, which is comprised of the 30S and 50S ribosomal subunits, is important for protein synthesis.

Models of protein synthesis assume that once the aminoacyl-tRNA is bound to the ribosomal A-site of the 70S ribosome complex, peptidyltransferase, an integral part of the 50S ribosomal subunit, can condense all twenty-one aminoacyl-tRNAs with equal efficiency, without intervention of exogenous proteins and GTP. However, several studies indicate that in vitro, the peptidyltransferase condenses predominantly hydrophobic amino acids. Peptide bond synthesis in vitro is also dependent upon aminoacyl moieties. In particular, prokaryotic 70S ribosomes cannot efficiently incorporate certain amino acids into polypeptides from cytidyl aminoacyl-adenosine (CA) (analogues of the 3'-terminal end of aminoacyl-tRNAs). As well, several antibiotics, such as anisomycin and chloramphenicol, inhibit peptide bond synthesis with some aminoacyl-tRNAs and not with others.

A prokaryotic gene encoding one of several known types of elongation factor proteins, elongation factor p (efp) was cloned and sequenced. Aoki et al., *Nucleic Acids Research*, 1991 (19), pp. 6215–6220, the disclosure of which is incorporated herein by reference in its entirety. Efp has been found to be essential for cell viability. Efp stimulates the efficiency of the peptidyltransferase activity of procaryotic ribosomes between fMet-tRNA$_f^{Met}$ and analogues of various aminoacyl-tRNAs. For example, the K' for the cytidyl(3'-5')-[2'(3')-O-L-CA-Gly is enhanced 50-fold, whereas that for CA-Phe is essentially unaltered by efp. Efp may modulate the efficiency of protein synthesis by controlling the rate of synthesis of certain peptide bonds. There are 800–900 molecules of efp per *E. coli*, or about 0.1 to 0.2 copy per ribosome, suggesting that efp may function catalytically in the cell. The preparation and isolation of efp can be found in M. C. Ganoza et al., *Eur. J. Biochem.*, 1985, vol. 146, pp. 287–294, and/or D-G. Chung et al. Chapter 4, pp. 69–80 of Ribosomes and Protein Synthesis, A Practical Approach, edited by G. Spedding, 1990, IRL Press at Oxford University Press, Oxford, N.Y. and Tokyo, the disclosures of which are incorporated herein by reference in their entirety.

The requirements of peptide-bond and ester-bond formation stimulated by efp have been studied with fMet-tRNA$_f^{Met}$ bound to 30S subunits and native or reconstituted 50S subunits. Efp functions in both peptide- and ester-bond synthesis promoted by the peptidyltransferase. The L16 protein (N-terminal fragment) of the 50S subunit is required for the efp-mediated synthesis of peptide bonds, whereas the L11, L15, and L7/L12 are not required in this reaction, suggesting that efp may function at a different ribosomal site than most other translation factors.

Of interest is the fact that efp differentially stimulates peptide bond synthesis when various amino acids are covalently linked to aminoacyl-adenosine (CA). It is possible that efp preferentially acts on weak acceptors for the peptidyltransferase. The specific mechanism whereby efp stimulates bond synthesis is not entirely clear. Efp may help accommodate fMet-tRNA$_f^{Met}$ or peptidyl-tRNAs, or both, within the active center of the peptidyltransferase or it could affect peptidyltransferase directly.

The position occupied by each species of aminoacyl-tRNA on the ribosomes has been studied using antibiotics that are known to inhibit specific sites on the ribosome. Two types of A sites can be distinguished by their different reactivities towards specific antibiotics. The first site (of the i type) occur after fMet-tRNA$_f^{Met}$ has directly entered the ribosomal P-site, where the E-site is free. The second A-site (of the e type) is the one normally used to bind aminoacyl-tRNAs to 70S ribosomes during the course of chain elongation.

The antibiotics neomycin, thiostrepton, and hygromycin appear to inhibit translocation and occupation of the A site, but they inhibit only about 20% or have no effect on efp reaction. These antibiotics also have no effect on formation of the fMet-tRNA$_f^{Met}$/ribosome translation complex nor on the peptide-bond synthesis which occurs in the absence of efp.

Streptomycin at $2 \times 10^{-5}$ M, which causes misreading and also inhibits A-site occupation of the e type, is a potent inhibitor of the efp-mediated reaction. The efp-mediated reaction is one in which purified efp is added to a translation complex of fMet-tRNA$_f^{Met}$: 70S ribosome:mRNA; and then puromycin or an appropriate amino acid-charged tRNA is added. Efp mediates the formation of a peptide bond between the fmet and the second amino acid. Streptomycin is known to interact with two sites on the 16S rRNA of the 30S subunit. It is unknown, however, whether streptomycin acts to directly inhibit efp.

Lincomycin inhibits peptidyltransferase and occupation of the A-site of the e type. Lincomycin has marginal effects on the synthesis of polyphenylalanine, but inhibits the puromycin reaction and nullifies the ability of efp to stimulate synthesis of peptide bonds. Erythromycin, also inhibits peptidyltransferase and it destabilizes the peptidyl-tRNA/ribosome/mRNA complex but it has no apparent effect on the efp reaction at $5 \times 10^{-5}$.

The present invention involves the surprising discovery of the critical role that efp may have in the procaryotic cell, and its role as a key component in the search for novel antimicrobial agents. These and other aspects of the invention are described below.

SUMMARY OF THE INVENTION

There is a need for more rapid and direct methods to screen compounds which may modulate ribosome mediated peptide bond formation. Such screening assays may discover new and useful antibiotics. New screens to detect and characterize compounds that affect efp and its functioning in the 70S ribosome, the 50S and 30S ribosomal subunits, and related proteins are disclosed herein. Newly discovered compounds or agents may promote cell death. The new understanding of the mechanism of action of known antimicrobials disclosed here may extend the usefulness of those antimicrobial agents.

Because of the surprising discovery disclosed here for the critical role that efp plays in the procaryotic cell, we can now disclose several aspects of this invention. Described herein are new methods or procedures to screen for, detect and/or characterize new compounds that modulate the function of efp in the prokaryotic cell. These methods or procedures include new in vitro methods as well as new in vivo methods.

In some embodiments of the invention, methods for identifying a compound which modulates activity of a prokaryotic elongation factor p in an in vitro assay, a cell based assay to determine the affect of the compound on cell function, a cell free extract assay to determine the affect of the compound on cell function are provided. The in vitro assay preferably comprises the steps of exposing elongation factor p with a compound, determining whether the compound modifies activity of the elongation factor p, and the cell-based assay preferably comprises determining whether the compound modifies activity of cell function. In some embodiments of the invention, the in vitro assay comprises determining whether the activity of the elongation factor p is decreased, determining whether the elongation factor p binds to the compound, determining whether the compound interferes with a function of the elongation factor p, or determining whether the compound interferes with a protein essential to the function of the elongation factor p such as the protein known as L16, or determining whether the compound binds to the ribosome or some component thereof that prevents the binding of efp to the ribosome and therefore interferes with the proper functioning of efp. In some embodiments of the invention, the step comprises measuring association of the compound with elongation factor p. In some embodiments of the invention, disclosures are to methods for determining whether a compound decreases a function of the cell.

Also disclosed herein are new methods or procedures to screen for, detect and/or characterize new compounds that modulate the function of the 30S ribosomal subunit when it interacts with efp in the prokaryotic cell. These methods or procedures include new in vitro methods as well as new in vivo methods.

In some embodiments of the invention, disclosures are to methods for determining whether a compound modulates the function of the 30S ribosome, this can be accomplished in a variety of ways, including but not limited to determining whether the compound inhibits binding of fmet-tRNA or mRNA to the 70S ribosome; determining whether the compound prevents the 50S subunit from binding to the 30S subunit, thereby preventing formation of a functional 70S ribosome; determining whether the compound inhibits the binding of any aminoacyl-tRNA to the ribosome; and determining whether a compound prevents the binding of initiation factor 1, initiation factor 2, initiation factor 3, or other factors necessary for formation of the initiation of the initiation complex or first peptide bond synthesis. In some embodiments of the invention, under in vitro conditions, the third step comprises measuring the presence of initiation complex in the cell, wherein a decrease in the amount of the complex confirms that the compound interferes with the interaction of efp and the 30S ribosome. In some embodiments, the third step comprises measuring affinity or displacement of fmet-tRNA to the complex, wherein a low affinity indicates that the compound interacts with the 30S complex containing elongation factor p. Following these procedures the compounds can then be exposed to cell based assays to determine the viability of the cells treated with the compounds.

Also disclosed herein are new methods or procedures to screen for, detect and/or characterize new compounds that modulate the function of the 50S ribosomal subunit when it interacts with efp in the prokaryotic cell. These methods or procedures include new in vitro methods as well as new in vivo methods.

In some embodiments of the invention, disclosures are to methods for determining whether a compound modulates the function of the 50S ribosome, this can be accomplished in a variety of ways, including but not limited to determining whether the compound inhibits binding of fmet-tRNA or mRNA to the 70S ribosome; determining whether the compound inhibits formation of the first peptide bond between fmet and the second amino acid; determining whether the compound prevents the 50S subunit from binding to the 30S subunit, thereby preventing formation of a functional 70S ribosome; determining whether the compound inhibits the binding of any aminoacyl-tRNA to the ribosome; and determining whether a compound prevents the binding of initiation factor 1, initiation factor 2, initiation factor 3, or other factors necessary for formation of the initiation of the initiation complex or first peptide bond synthesis. In some embodiments of the invention, under in vitro conditions, the third step comprises measuring the presence of initiation complex in the cell, wherein a decrease in the amount of the complex confirms that the compound interferes with the interaction of efp and the 50S ribosome. In some embodiments of the invention, the third step comprises measuring affinity or displacement of fmet-tRNA to the complex, wherein a low affinity indicates that the compound interacts with the 50S complex containing elongation factor p. Following these procedures the compounds can then be exposed to cell-based assays to determine the viability of the cells treated with the compounds.

Also disclosed herein are new methods or procedures to screen for, detect and/or characterize new compounds that modulate the function of the 70S ribosome when it interacts with efp in the prokaryotic cell. These methods or procedures include new in vitro methods as well as new in vivo methods.

In some embodiments of the invention, disclosures are to methods for determining whether a compound modulates the function of the 70S ribosome, this can be accomplished in a variety of ways, including but not limited to including but not limited to determining whether the compound inhibits binding of fmet-tRNA or mRNA to the 70S ribosome; determining whether the compound inhibits formation of the first peptide bond between fmet and the second amino acid; determining whether the compound prevents the 50S subunit from binding to the 30S subunit, thereby preventing formation of a functional 70S ribosome; determining whether the compound inhibits the binding of any aminoacyl-tRNA to the ribosome; and determining whether a compound prevents the binding of initiation factor 1, initiation factor 2, initiation factor 3, or other factors necessary for formation of the initiation of the initiation complex or first peptide bond synthesis. In some embodiments of the invention, the third step comprises measuring the presence of initiation complex, wherein a decrease in the amount of the complex confirms that the compound interferes with the interaction of efp and the 70S ribosome. In some embodiments of the invention, the third step comprises measuring affinity or displacement of fmet-tRNA to the complex, wherein a low affinity indicates that the compound interacts with the 70S complex containing elongation factor p. Following these procedures the compounds can then be exposed to cell-based assays to determine the viability of the cells treated with the compounds.

In some embodiments of the invention a eukaryote protein known as eIF5A, a protein that performs a similar function in eukaryote cells as the efp protein does in prokaryotic cells is used to further identify and characterize compounds that have little or no modulating effect or inhibiting effect on eIF5A but that do modulate or inhibit efp. New methods or procedures, that employ all of the methods described above, to detect or characterize a new compound are then combined with the additional steps of determining that compounds modulating activity on the eukaryote version of efp (or eIF5A) and then comparing the modulating activity of the newly identified compound on prokaryotic efp with its modulating activity on eIF5A in order to identify or characterize compounds that inhibit efp activity on prokaryotic cells but have little adverse affect on the activity of eIF5A.

Also disclosed herein are new methods or procedures that allow the inhibition or control the growth of microbial organisms. Methods which disclose compounds that modulate the function of efp in the prokaryotic cell.

One important aspect of this invention is the discovery of the use of known compounds that can now be used to interfere with the important function of the efp protein.

The present invention further provides methods of modulating the activity of a bacterial elongation factor p comprising contacting the protein or a cell containing the protein with an oxazolidinone compound.

The present invention further provides methods of modulating the activity of a bacterial 30S ribosomal subunit comprising contacting the protein or a cell containing the subunit with an oxazolidinone.

The present invention further provides methods of modulating the activity of a bacterial 50S ribosomal subunit comprising contacting the protein or a cell containing the subunit with an oxazolidinone.

The present invention further provides methods of modulating the activity of a bacterial 70S ribosome comprising contacting the protein or a cell containing the subunit with an oxazolidinone.

The present invention further provides methods of modulating the activity of a bacterial L16 protein comprising contacting the protein or a cell containing the subunit with an oxazolidinone.

The present invention further provides methods of modulating the activity of a bacterial elongation factor p comprising contacting the protein or a cell containing the protein with an oxazolidinone type of compound.

These and other aspects of the invention are described in greater detail below.

DETAILED DESCRIPTION OF PREFERRED EMBODIMENTS

Various definitions are made throughout this document. Most words have the meaning that would be attributed to those words by one skilled in the art. Words specifically defined either below or elsewhere in this document have the meaning provided in the context of invention as a whole and as are typically understood by those skilled in the art.

As used herein, the term "activity" refers to a variety of measurable indicia suggesting or revealing binding, either direct or indirect; affecting a response, i.e. having a measurable affect in response to some exposure or stimulus, including, for example, the affinity of the compound for directly binding efp or aribosome, or, for example, measurement of amounts of upstream or downstream proteins or other similar functions after some stimulus or event.

As used herein, the term "affects" means either a decrease or increase in the amount or quality of a particular cell function in response to some stimulus, exposure or event.

As used herein, the term "binding" means the physical interaction between two proteins or compounds or associated proteins or compounds or combinations thereof. Binding includes ionic, non-ionic, Hydrogen bonds, Van der Waals, hydrophobic interactions, etc. The physical interaction, the binding, can be either direct or indirect, indirect being through or because of another protein or compound. Direct binding refers to interactions that do not take place through or because of another protein or compound but instead are without other substantial chemical intermediates.

As used herein, the phrase "cell function" is defined to include all aspects of functionality of cells including cell viability but, especially, cell growth.

As used herein, the term "compound" means any identifiable chemical or molecule, small molecule, peptide, protein, sugar, natural or synthetic, or a discrete agent such as a specific amount of light, energy or temperature that is suspected to potentially interact with the process or system of interest, here typically efp, 30S, 50S, 70S ribosomes and related proteins.

As used herein, the term "contacting" means either direct or indirect, in vitro or in vivo administration of a compound to target, where the target may be a protein, ribosome, portion of a cellular system, whole cell, tissue, or mammal. The target may be in an in vitro or in vivo system with any number of buffers, salts, solutions etc.

As used herein, the phrases and terms "elongation factor p", "efp", "ef-p", "EFP", or "EF-P" refers to the prokaryotic protein having a function like that of the efp protein isolated from *E. coli* or various other bacteria or recombinant versions of that protein such as that described by M. C. Ganoza et al., *Eur. J Biochem* 1985, vol. 146, pp. 287–294, and H. Aoki et al. *Biochimie* (1997) vol.79, pp. 7–11, Aoki et al., *Nucleic Acids Research*, 1991 (19), pp.6215–6220, the disclosures of which are incorporated herein by reference in their entirety. The nucleic acid sequence of one or more of such proteins are provided in the references and the specification below. The EF-P differs from EF-Tu and EF-G in that it does not require GTP for its activity. Efp can be cloned, synthesized, or otherwise manipulated and if a version is made active according to any of the screens described here or in the references cited then that protein should be considered an efp protein.

As used herein, the term "effects" means either a decrease or increase in the amount or quality of a particular cell function in response to some stimulus, exposure or event.

As used herein, the phrase "first peptide bond reaction" means the joining of the I carboxyl group of formylmethionine to the I amino group of another amino acid.

As used herein, the phrase "formation of the initiation complex" means formation of a complex containing N formylmethionyl tRNA, 30S subunit, mRNA, GTP and the initiation factors IF1, IF2 and IF3.

As used herein, the term "interacting" means direct binding, including selective or specific binding, to a constituent of the ribosomal complex such that cell function is effected.

As used herein, the term "L16" means the L16 prokaryotic protein involved in bacterial protein synthesis as described in H. Aoki, et al., *Molecular Characterization of the Procaryotic Efp Gene Product Involved in a Peptidyltransferase Reaction, Biochimie* (1997) vol. 79, pp. 7–11, the disclosure of which is incorporated herein by reference in its entirety.

As used herein, the terms "modulates" or "modifies" means an increase or decrease in the amount, quality, or effect of a particular activity or protein.

As used herein, the phrase "70S ribosome" means a prokaryotic ribonucleoprotein particle with a sedimentation coefficient of 70S that can be dissociated into a large subunit of 50S and a small subunit of 30S.

As used herein, the phrase "50S ribosome" or "50S subunit" means a prokaryotic ribonucleoprotein particle with a sedimentation coefficient of 50S that can be dissociated from a 70S ribosome.

As used herein, the phrase "30S ribosome" or "30S subunit" means a prokaryotic ribonucleoprotein particle with a sedimentation coefficient of 30S that can be dissociated from a 70S ribosome.

As used herein, the phrase "peptide bond donor" means any compound that has a free amino group capable of forming a peptide bond with an amino acid. Preferred peptide bond donors include, but are not limited to, puromycin or a puromycin analog, or any amino acyl-tRNA or an analog of amino acyl-tRNA.

As used herein, the term "oxazolidinone" means a compound of the class known as oxazolidinones, including the compounds described in U.S. Ser. Nos. 07/438,759, 07/553, 795, 08/006,596, 07/882,407, 07/786,107, 07/831,213, 08/233,903, 08/119,279, 08/226,158, 08/155,988, 08/329, 717, 07/909,387, 08/339,979, 08/384,278, 08/875,800, 07/880,432, 08/610,031, 08/332,822, 07/988,589, 08/003, 778, 08/066,356, 08/438,705, 60/015,499, 60/003,149, 09/138,205, 09/138,209, 08/696,313, 60/012,316, 08/803, 469, 60/003,838, 08/709,998, 60/008,554, 08/762,478, 60/007,371, 08/850,424, 60/048,342, 09/080,751, 60/052, 907, 60/064,746, 09/111,995, 60/064,738, 60/065,376, 60/067,830, 60/089,498, 60/100,185, 09/081,164, 60/088, 283, 60/092,765, 07/244,988, 07/253,850; European Patents EP 0500686, EP 0610265, EP 0673370; PCT Application Numbers PCT/US90/06220, PCT/US94/08904, PCT/US94/ 10582, PCT/US95/02972, PCT/US95/10992, PCT/US93/ 04850, PCT/US95/12751, PCT/US96/00718, PCT/US93/ 03570, PCT/US93/09589, PCT/US96/05202, PCT/US97/ 03458, PCT/US96/12766, PCT/US97/01970, PCT/US96/ 14135, PCT/US96/19149, PCT/US96/17120, PCT/US98/ 09889, PCT/US98/13437; and U.S. Pat. Nos. 5,700,799, 5,719,154, 5,547,950, 5,523,403, 5,668,286, 5,652,238, 5,688,792, 5,247,090, 5,231,188, 5,654,428, 5,654,435, 5,756,732, 5,164,510, 5,182,403, 5,225,565, 5,618,949, 5,627,197, 5,534,636, 5,532,261, 5,776,937, 5,529,998, 5,684,023, 5,627,181, 5,698,574, 5,220,011, 5,208,329, 5,036,092, 4,965,268, 4,921,869, 4,948,801, 5,043,443, 5,130,316, 5,254,577, 4,877,892, 4,791,207, 4,642,351, 4,665,171, 4,734,495, 4,775,752, 4,870,169, 4,668,517, 4,340,606, 4,362,866, 4,193,918, 4,000,293, 3,947,465, 4,007,168, 3,674,780, 3,686,170, 3,906,101, 3,678,040, 3,177,114, 3,141,889, 3,149,119, 3,117,122, 5,719,154, 5,254,577, 4,801,600, 4,705,799, 4,461,773, 4,243,801, 3,794,665, 3,632,577, 3,598,830, 3,513,238, 3,598,812, 3,546,241, 3,318,878, 3,322,712; the disclosures of which are incorporated herein by reference in their entirety. Preferred oxazolidinones include linezolid and eperezolid.

The description of this invention is organized into several parts. The different parts and not exclusive of each other, they all describe one invention but different aspects and applications of the invention will be emphasized and described in greater or lesser detail in the different parts of the description. One part will emphasize the methods and procedures whereby efp is used as molecular target to find, identify or characterize compounds that modulate the activity of efp, especially compounds that interfere or inhibit that activity. A subportion describes in vitro methods of evaluating efp and in vivo applications thereof. Other parts are structured similarly to the first part and conceptually should include the first part, only emphasis and methods directed to the 30S ribosomal subunit, the 50S ribosomal subunit, and the 70S ribosome are described in these other parts. Another part refers to and includes using the methods and procedures and the information in the other parts and applying it in a novel fashion, which is to add the additional procedure of comparing the information of the first parts to with similar information about the compounds identified from steps previously identified to a similar study of the activity of those compounds on eIF5A. Another part describes compounds that are now known to have expected activity against the prokaryotic functions and systems described in the previously described parts.

The present invention is directed, in part, to methods for identifying compounds which modulate activity of efp or translation initiation complex when interacting with efp. In addition, the methods of the present invention also include, in a similar manner, identifying compounds which modulate activity of prokaryotic 30S subunit, 50S subunit, and 70S subunit of the ribosome.

Efp, as well as the other components described above, can be isolated from a natural source such as, for example, a bacteria, like *E. coli* or various other bacteria, such as, for example *S. aureus, S. pneumoniae, H. influenzae,* and an Enterococcus species. In addition, recombinant versions of these proteins, such as that described by M. C. Ganoza et al, *Eur. J Biochem* 1985, vol. 146, pp.287–294, and H. Aoki et al. *Biochimie* (1997) vol. 79, pp. 7–11, Aoki et al., *Nucleic Acids Research*, 1991 (19), pp. 6215–6220, the disclosures of which are incorporated herein by reference in their entirety, can be prepared. One skilled in the art is readily able to prepare such recombinant proteins.

In a preferred embodiment the efp can be a recombinant protein having post-translation modifications, such as, for example, those modifications selected from the group consisting of efp proteins where the lysine residues are modified. Recombinant proteins can be prepared in eukaryotic systems such as, for example, using the baculovirus expression vectors which are well known to the skilled artisan.

The preferred form of efp is the native form of the protein purified from S. aureus, E. coli or other pathogenic bacteria. However, according to the present invention, other forms of efp include the native form of the protein purified from various gram positive bacterial pathogens, including: *Staphylococcus aureus; Staphylococcus epidermidis* (A, B, C biotypes); *Staphylococcus caseolyticus; Staphylococcus gallinarum; Staphylococcus haemolyticus; Staphylococcus hominis; Staphylococcus saprophyticus; Streptococcus agalactiae* (group B); *Streptococcus mutans*/rattus; *Streptococcus pneumoniae; Streptococcus pyogenes* (group A); *Streptococcus salivarius; Streptococcus sanguis; Streptococcus sobrinus;* Actinomyces spps.; *Arthrobacterhistidinolovorans; Corynebacterium diptheriae; Clostridium difficle;* Clostridium spps.; *Enterococcus casseliflavus; Enterococcus durans; Enterococcus faecalis; Enterococcus faecium;*

*Enterococcus gallinarum; Erysipelothrix rhusiopathiae; Fusobacterium* spps.; *Listeria monocytogenes*; Prevotella spps.; *Propionibacterium acnes*; and *Porphyromonas gingivalis*.

Still other forms of efp include the native form of the protein purified from various gram negative bacterial pathogens, including: *Acinetobacter calcoaceticus; Acinetobacter haemolyticus; Aeromonas hydrophila; Bordetella pertussis; Bordetella parapertussis; Bordetella bronchiseptica; Bacteroides fragilis; Bartonella bacilliformis; Brucella abortus; Brucella melitensis; Campylobacter fetus; Campylobacter jejuni; Chlamydia pneumoniae; Chlamydia psittaci; Chlamydia trachomatis; Citrobacterfreundii; Coxiella burnetti; Edwardsiella tarda; Edwardsiella hoshinae; Enterobacter aerogenes, Enterobacter cloacae* (groups A and B); *Escherichia coli* (to include all pathogenic subtypes) Ehrlicia spps.; *Francisella tularensis; Haemophilus actinomycetemcomitans; Haemophilus ducreyi; Haemophilus haemolyticus; Haemophilus influenzae; Haemophilus parahaemolyticus; Haemophilusparainfluenzae; Hafnia alvei; Helicobacterpylori; Kingella kingae; Klebsiella oxytoca; Klebsiella pneumoniae; Legionella pneumophila;* Legionella spps.; Morganella spps.; *Moraxella cattarhalis; Neisseria gonorrhoeae; Neisseria meningitidis; Plesiomonas shigelloides; Proteus mirabilis; Proteus penneri;* Providencia spps.; *Pseudomonas aeruginosa; Pseudomonas species; Rickettsia prowazekii; Rickettsia rickettsii; Rickettsia tsutsugamushi*; Rochalimaea spps.; Salmonella subgroup 1 serotypes (to include *S. paratyphi* and *S. typhi*); Salmonella subgroups 2, 3a, 3b, 4, and 5; *Serratia marcesans*; Serratia spps.; *Shigella boydii; Shigellaflexneri; Shigella dysenteriae; Shigella sonnei; Yersinia enterocolitica; Yersiniapestis; Yersiniapseudotuberculosis; Vibrio cholerae; Vibrio vulnificus;* and *Vibrio parahaemolyticus*.

Still other forms of efp include the native form of the protein purified from various Mycobacterial species, including: *Mycobacterium tuberculosis; Mycobacterium avium*; and other Mycobacterium spps.

Still other forms of efp include the native form of the protein purified from various Mycoplasmas (or pleuropneumonia-like organisms), including: *Mycoplasma genitalium; Mycoplasma pneumoniae*; and other Mycoplasma spps.

Still other forms of efp include the native form of the protein purified from various Treponemataceae (spiral organisms), including: *Borrelia burgdoreri*; other Borrelia species; Leptospira spps.; *Treponema pallidum*.

*S. aureus* efp is defined as a protein having an amino acid sequence with at least about 70% homology determined by, for example, alignment and direct one-to-one correspondence with the following protein sequence MISVNDFKTG LTISVDNAIW KVIDFQHVKP GKGSAFVRSK LRNLRTGAIQ EKTFRAGEKV EPAMIENRRM QYLYADGDNH VFMDNESFEQ TELSSDYLKE ELNYLKEGME VQIQ-TYEGET IGVELPKTVE LTVTETEPGI KGDTATGATK SATVETGYTL NVPLFVNEGD VLIINTGDGS YISRG (SEQ ID NO: 1) and having activity in the efp activity assay described below.

*E. coli* efp is defined as a protein having an amino acid sequence with at least about 70% homology, determined as described above, with the following sequence MATYYSNDFRA GLKIMLDGEP YAVEASEFVK PGKGQAFARV KLRRLLTGTR VEKTFKSTDS AEGAD-VVDMN LTYLYNDGEF WHFMNNETFE QLSADA-KAIG DNAKWLLDQA ECIVTLWNGQ PISVTPPNFV ELEIVDTDPG LKGDTAGTGG KPATLSTGAV VKV-PLFVQIG EVIKVDTRSG EYVSRVK (SEQ ID NO:2) and having activity in the efp activity assay described below.

In preferred embodiments, in order to identify compounds which modulate efp activity or activity of any of the other components of the ribosome described above, in vitro assays are disclosed, wherein, for example, cell-free extract comprising efp (as well as any of the other components described above; 30S, 50S, and 70S) and the translation initiation complex, or components thereof, is contacted with a test compound. The contacting can take place in buffers or media well known to those skilled in the art. In addition, varying amounts of the test compound can be used as desired by the practitioner. Test compounds provided herein, including those identified by the present methods, can be formulated into pharmaceutical compositions by, for example, admixture with pharmaceutically acceptable nontoxic excipients and carriers. Test compounds which test positive can be used as antiseptic agents. Accordingly, the methods of the present invention also include a method of identifying antiseptic agents.

In some embodiments of the invention, a method for identifying a compound which modulates the activity of prokaryotic efp comprises preparing a solution of efp; contacting the solution containing efp with the compound; and determining whether the compound modifies activity of efp. Whether the compound modifies the activity of the efp is determined by, for example, determining whether the compound binds to efp. Binding can be determined by employing a number of art-recognized procedures.

Determining whether the compound binds to efp can be accomplished by a binding assay including, but not limited to, gel-shift mobility electrophoresis, Western blot, filter binding, and scintillation proximity assay. U.S. Pat. No. 4,568,649, which is disclosed herein by reference in its entirety, teaches a scintillation proximity assay. Additional information regarding scintillation proximity assay systems and applications is available from Amersham Pharmacia Biotech (UK, Little Chalfont, Buckinghamshire, England HP79NA).

Determining whether the compound binds to efp can also be accomplished by measuring the intrinsic fluorescence of efp and determining whether the intrinsic fluorescence is modulated in the presence of the compound. Preferably, the intrinsic fluorescence of efp is measured as a function of the tryptophan residue(s) of efp. Preferably, fluorescence of efp is measured and compared to the fluorescence intensity of efp in the presence of the compound, wherein a decrease in fluorescence intensity indicates binding of the compound to efp. Preferred methodology is set forth in "Principles of Fluorescence Spectroscopy" by Joseph R. Lakowicz, New York, Plenum Press, 1983 (ISBN 0306412853) and "Spectrophotometry And Spectrofluorometry" by C. L. Bashford and D. A. Harris Oxford, Washington D.C., IRL Press, 1987 (ISBN 0947946691), the disclosures of which are incorporated herein by reference in their entirety.

In other embodiments of the invention, the method described above further comprises determining whether the compound interfering with the function of efp is interfering with other protein(s) essential for the functioning of efp. Preferably, the other protein essential for the functioning of efp is L16 protein.

In other embodiments of the invention, a method for identifying a compound which modulates the activity of prokaryotic efp comprises preparing a solution of efp; contacting the solution of efp with a radiolabeled oxazolidinone, isolating or measuring the radiolabeled oxazolidinone bound to efp; contacting the compound with the radiolabeled oxazolidinone bound to efp; and determining whether the compound displaces the radiolabeled oxazolidinone from efp. Additionally, the method may further comprise measuring the displacement of the radiolabeled oxazolidinone from efp. Preferably, determination of displacement is accomplished by comparing the amount of the detectable radiolabel in the solution prior to addition of the compound with the amount of detectable radiolabel in the solution after addition of the compound, wherein a decrease in detectable radiolabel indicates that the compound displaces the radiolabeled oxazolidinone compound from the complex. Radiolabeled competitive binding studies are described in A. H. Lin et al. *Antimicrobial Agents and Chemotherapy*, 1997, vol.41, no.10. pp.2127–2131, the disclosure of which is incorporated herein by reference in its entirety. Preferably, the radiolabeled oxazolidinone compound is linezolid or eperezolid.

In some embodiments, the activity of the efp-mediated activity (or activity of any of the other ribosomal components described above) can be measured by the amount of translation initiation complex formed. One skilled in the art is readily familiar with measuring the amount of translation initiation complex formed. A compound that inhibits efp will be reflected in the amount of translation initiation complex formed in vitro. Preferably, the method comprises preparing a first solution of efp; preparing a second solution comprising N-formylmethionyl-tRNA (fMet-tRNA), 30S subunit, 50S subunit, any mRNA containing an AUG sequence, and initiation factors 1, 2, and 3; contacting the second solution with the first solution and the compound; and determining whether the compound allows fMet-tRNA to bind to a complex formed through the interaction of efp, 30S subunit, 50S subunit, any mRNA containing an AUG sequence, and initiation factors 1, 2, and 3. Efp-mediated activity (or activity of any of the other ribosomal components described above) can be measured by measuring affinity or displacement of fMet-tRNA to said complex. A compound that inhibits the binding of fMet-tRNA to ribosomal complexes containing efp will be reflected in the amount of fMet-tRNA bound to the complex. The lower the amount of fMet-tRNA bound, the greater the inhibitory affect the test compound has. This type of affinity displacement is described by S. M. Swaney, et al. *Antimicrobial Agents and Chemotherapy* (1998) vol. 42, no. 12, pp.3251–3255, the disclosure of which is incorporated herein by reference in its entirety. Using ordinary skills and techniques in the art the procedures in this reference can be easily adapted to the invention described herein. Preferably, the mRNA containing an AUG sequence consists essentially of rArUrG. Preferably, efp is isolated from a natural source, such as a prokaryotic organism, preferably a bacteria including, but not limited to, *E. coli, S. aureus, S. pneumoniae, H. influenzae*, or an Enterococcus species. In all of the tests described herein, one skilled in the art can use fragments of mRNA of any length as long as the fragment comprises an AUG sequence.

In other embodiments of the invention, a method for identifying a compound which modulates the activity of efp comprises contacting a cell containing efp in vitro with a compound identified by the methods described above, and determining whether the compound inhibits cell growth. Alternately, the contacting can take place in vivo, in which an animal, such as, for example, a mammal or mouse or other suitable animal known to those skilled in the art, is contacted by administering a pharmaceutical composition comprising the test compound and pharmaceutically acceptable salt, carrier, or diluent. In addition, varying numbers of cells and concentrations of test compounds can be used. Whether the test compound increases or decreases activity of the efp is determined. In addition, whether the test compound promotes cell survival or cell death is also determined. The test compound can be administered to a mammal topically, intradermally, intravenously, intramuscularly, intraperitonally, subcutaneously, and intraosseously, or any other desired route and can be in any amount desired by the practitioner. Determination of the susceptibility of bacteria to particular compounds can be determined according to the methods described in National Committee for Clinical Laboratory Standards, 1993, Approved standard, Methods for dilution antimicrobial susceptibility tests for bacteria that grow aerobically, $_3$rd Ed., National Committee for Clinical Laboratory Standards, Villanova, Pa., the disclosure of which is incorporated herein by reference in its entirety.

In other embodiments of the invention, each of the above-described methods can be applied to compositions of efp which also contain either the 30S subunit, 50S subunit, or 70S ribosome. For example, in some embodiments of the invention, a method for identifying a compound which modulates the activity of prokaryotic efp comprises preparing a composition or solution of efp; adding prokaryotic 30S subunit (or 50S subunit or 70S ribosome) to the solution of efp; contacting the compound with the composition or solution of efp and 30S subunit (or 50S subunit or 70S ribosome); and determining whether the compound binds to efp in association with the 30S subunit (or 50S subunit or 70S ribosome) or whether the compound interferes with the binding of said efp and said 30S subunit (or 50S subunit or 70S ribosome). In some embodiments, determining whether the compound binds to efp in association with the 30S subunit (or 50S subunit or 70S ribosome) or whether the compound interferes with the binding of said efp and said 30S subunit (or 50S subunit or 70S ribosome) comprising determining whether the compound binds to the 30S subunit (or 50S subunit or 70S ribosome) or efp. In some embodiments, the intrinsic fluorescence of efp bound to said 30S subunit (or 50S subunit or 70S ribosome) is measured, as described above, and whether the intrinsic fluorescence is modulated by the compound is determined. Preferably, the intrinsic fluorescence of efp is measured as a function of changes in the fluorescence of the tryptophan residue(s) of efp, as described above. In addition, the above-described method may further comprise determining whether the compound interfering with the function of efp is interfering with other protein(s), such as L16 protein, essential for the functioning of efp. Determination of binding can be accomplished in the same manner as described above. In addition, competitive binding assays using a solution of efp and 30S subunit (or 50S subunit or 70S ribosome) with a radiolabeled oxazolidinone and a test compound can be performed essentially as described above.

In other embodiments of the invention, a method for identifying a compound which modulates the activity of prokaryotic efp comprises preparing a solution of radiolabeled efp; adding a 30S subunit (or 50S subunit or 70S ribosome) and the compound with the solution of radiolabeled efp; measure whether the 30S subunit (or 50S subunit or 70S ribosome) is bound to radiolabeled efp; and if the 30S subunit (or 50S subunit or 70S ribosome) is not bound to efp, then select the compounds which interfered with the binding thereof. Preferably, determination of binding is accomplished by employing a binding assay described above.

In other embodiments of the invention, a method for identifying a compound which modulates the activity of prokaryotic efp comprises preparing a first solution of efp;

preparing a second solution comprising N-formylmethionyl-tRNA (fMet-tRNA), 30S subunit (or 50S subunit or 70S ribosome), any mRNA containing an AUG sequence, and initiation factors 1, 2, and 3; and contacting the second solution with the first solution and the compound; and determining whether the compounds allows fMet-tRNA to bind to a complex formed through the interaction of efp, 30S subunit (or 50S subunit or 70S ribosome), any mRNA containing the AUG sequence, and initiation factors 1, 2, and 3. Preferably, the mRNA containing an AUG sequence consists essentially of rArUrG. Preferably, efp is isolated from a natural source, such as a prokaryotic organism, such as a bacteria including, but not limited to, *E. coli, S. aureus, S. pneumoniae, H. influenzae*, and an Enterococcus species.

In other embodiments of the invention, a method for identifying a compound which modulates the activity of prokaryotic efp comprises contacting a cell containing said efp and also the 30S subunit, 50S subunit or 70S ribosome with a compound identified by the previously described methods, and determining whether the compound inhibits cell growth, as described above.

In another embodiment, a method for identifying a compound which modulates the activity of prokaryotic efp comprises preparing a first solution of efp; preparing a second solution comprising 50S subunit or 70S ribosome, a tRNA fragment comprising CACCA-radiolabeled amino acid, and a peptide bond donor; contacting the second solution with the first solution and the compound; and determining whether the compound inhibits the first peptide bond reaction of a complex formed through the interaction of efp, 50S subunit or 70S ribosome, a tRNA fragment comprising CACCA-radiolabeled amino acid, and a peptide bond donor efp. Alternatively, the second solution can comprise N-formylmethionyl-tRNA (fMet-tRNA), 30S subunit, 50S subunit, any mRNA containing an AUG sequence, and initiation factors 1, 2, and 3, and a peptide bond donor, and it is determined whether the compound inhibits the first peptide bond reaction of a complex formed through the interaction of efp, fMet-tRNA, 30S subunit, 50S subunit, any mRNA containing an AUG sequence, and initiation factors 1, 2, and 3. A compound that inhibits efp (or any of the other ribosomal components described above) will be reflected in the amount of first peptide bond synthesis formed in vitro. For example, efp allows formation of a peptide bond between N-formylmethionine and the second amino acid (or puromycin as a substitute). Addition of a compound that inhibits the action of efp will prevent formation of the peptide bond, leaving the preformed initiation complex fMet-tRNA:70S ribosome:mRNA intact. M. C. Ganoza et al., *Eur. J Biochem* 1985, vol. 146, pp. 287–294, and/or D-G. Chung et al. Chapter 4, pp. 69–80 of Ribosomes and Protein Synthesis, A Practical Approach, edited by G. Spedding, 1990, IRL Press at Oxford University Press, Oxford, N.Y. and Tokyo, the disclosures of which are incorporated herein by reference in their entirety. The first peptide bond formation can also be determined according to the methods described in Monro, et al., *J. Mol. Biol.*, 1967, 25, 347–350, Monro, et al., *Methods Enzymol.*, 1971, 20, 472–481, the disclosures of which are incorporated herein by reference in their entirety. Preferably, the peptide bond donor includes, but is not limited to, puromycin and analogs thereof, and any amino acyl-tRNA and analogs thereof. Preferably, efp is isolated from a natural source, such as, for example, a prokaryotic organism, preferably, a bacteria, such as, for example, *E. coli, S. aureus, S. pneumoniae, H. influenzae*, or an *Enterococcus* species. The above described method can also be employed to identify a compound which inhibits the first peptide bond reaction of a complex formed through the interaction of efp, 50subunit or 70S ribosome, a tRNA fragment comprising CACCA-radiolabeled amino acid, and a peptide bond donor and efp. The above described method can also be employed to identify a compound which inhibits the first peptide bond reaction of a complex formed through the interaction of fMet-tRNA, 30S subunit, 50S subunit, any mRNA containing an AUG sequence, and initiation factors 1, 2, and 3, and a peptide bond donor and efp. In addition, one skilled in the art can determine whether the compound, identified as described above, inhibits cell growth by contacting a cell containing efp, or any other subunits or proteins described above.

In another embodiment, a method for identifying a compound which modulates the activity of prokaryotic efp comprises contacting a cell or solution containing efp with a detectably labeled oxazolidinone compound known to bind efp under conditions whereby efp forms a complex with the oxazolidinone compound; contacting the solution or cell with an unlabeled compound; and determining whether the unlabeled compound displaces the labeled oxazolidinone compound from the complex. Preferably, the cell or solution contains an oxazolidinone compound, a compound with a substantial binding affinity for efp, 30S, 50S, or 70S, L16 protein, or other components of the ribosome. Once the cell, or cell extract, or solution containing the components, is contacted with the test compound, the ribosomal complex containing the efp (and/or the other ribosome components described above) is isolated, and it is determined to what extent the test compound has displaced oxazolidinone. There are many techniques known in the art for determining displacement. Preferably, determination of displacement is accomplished by comparing the amount of the detectable label in the cell or solution prior to addition of the unlabeled compound with the amount of detectable label in the cell or solution after addition of unlabeled compound, wherein a decrease in detectable label indicates that the compound displaces the oxazolidinone compound from the complex. Preferably, the detectable label is a radiolabel or a fluorescent label. Radiolabeled competitive binding studies are described in A. H. Lin et al. *Antimicrobial Agents and Chemotherapy*, 1997, vol. 41, no. 10. pp. 2127–2131, the disclosure of which is incorporated herein by reference in its entirety. Fluorescent labeling is well know to the skilled artisan. Preferably, the oxazolidinone compound is linezolid or eperezolid.

In another embodiment of the invention, the test compound is further examined to determine whether it modulates the eukaryotic homolog of elongation factor p, eIF5A. eIF5A is described in Smit-McBride et al., *Sequence Determination and cDNA Cloning of Eukaryotic Initiation Factor 4D, the Hypusine-containing Protein*, (1989) *J. Biol. Chem.*, vol. 264, pp. 1578–1583, the disclosure of which is incorporated here in by reference in its entirety. A method for identifying a compound which modulates the activity of prokaryotic efp but not eukaryotic eIF5A preferably comprises initially determining whether the compound modulates the activity of prokaryotic efp by any of the methods described herein; followed by the steps of preparing a first composition or solution of eIF5A; preparing a second solution comprising methionyl-tRNA (Met-tRNA), 80S ribosome, any mRNA containing an AUG sequence, initiation factors eIF-2, eIF-3, eIF-5, eIF-4C, eIF-4D, and a peptide bond donor; contacting the second solution with the first solution and the compound; and determining whether the compound inhibits the first peptide bond reaction of a complex formed through the interaction of eIF5A, Met-tRNA, 80S ribosome, any mRNA containing an AUG sequence, and initiation factors eIF-2, eIF-3, eIF-5, eIF-4C, eIF-4D, as described above. Preferred peptide bond donors include, but are not limited to, puromycin and analogs thereof, and any amino acyl-tRNA and analogs thereof. Preferred mRNA sequences must include rArUrG, but may include additional nucleotides. Preferably, eIF5A is isolated from a natural source, such as a eukaryotic organism, preferably a mammal.

In some embodiments of the invention, this determination is made in a manner similar to the determination for prokaryotic efp except eukaryotic eIF5A is used. Preferably, compounds which modulate prokaryotic efp but not eukaryotic eIF5A are identified as described in K. Moldave, *Eukaryotic Protein Synthesis*, (1985) *Ann. Rev. Biochem*, vol.54, pp. 1109–1149, the disclosure of which is incorporated herein by reference in its entirety. In addition, first peptide bond formation can be analyzed as described in Benne et al., *J. Biol. Chem.*, 1978, 253, 3070–3087, the disclosure of which is incorporated herein by reference in its entirety.

The present invention is further directed to methods of modulating the activity of efp, 30S subunit, 50S subunit, or 70S subunit, L16 protein, or ribosomal subunits containing any of the same, or cells or cell preparations (including cell lysates) containing any of the same by contacting any of the above-described samples with an oxazolidinone compound. Contacting can be in vitro or in vivo by any of the routes of administration described above. The oxazolidinone can be formulated as described above into a pharmaceutical composition.

The invention is further illustrated by way of the following examples which are intended to elucidate the invention. These examples are not intended, nor are they to be construed, as limiting the scope of the disclosure.

EXAMPLES

Example 1

Assay to Identify Compounds that Bind to efp by Displacing a Bound Radiolabeled Oxazolidinone Materials. Unlabeled PNU 100592 10 mM, a nitrocellulose membrane such as, Millipore Immobilon-P$^{SQ}$ membrane (pre-treated with 70% ethanol and rinsed with deionized water).

The purification of the native efp protein has been described previously. Aoki et al. *Biochime* 1997, vol. 79, pp. 7–11. "Molecular characterization of the prokaryotic efp gene product involved in a peptidyl transferase reaction" and/or D-G. Chung et al. Chapter 4, pp. 69–80 of Ribosomes and Protein Synthesis, A Practical Approach, edited by G. Spedding, 1990, IRL Press at Oxford University Press, Oxford, N.Y. and Tokyo, both articles incorporated here by reference. Purification of efp can also be performed according to the methods of Aoki, et al., *Nuc. Acids Res.*, 1991, 19, 6215–6220, which is incorporated herein by reference in its entirety. Purification of efp can also be accomplished with an immunoaffinity column using antibodies directed against *E. coli* and *S. aureus* efp. Recombinant efp from *S. aureus* or *E. coli* is preferably expressed as a Histag fusion protein, expressed in *E. coli*, and purified via affinity column chromatography using Ni-NTA-Sepharose. Bound efp is preferably eluted in an imidazole gradient.

An efp reaction mixture (final concentrations in a reaction mixture of 100 µl) s prepared containing TKM Buffer (50 mM Tris, pH 7.5, 200 mM KCl, 5 mM magnesium acetate), Elongation factor P (EFP) 0.192 mg/ml or 9 µM, radiolabeled $C^{14}$-linezolid or $C^{14}$-eperezolid 10 µM (stock 24.3 mCi/mmol, 59.32 µCi/mg) or $H^3$-eperezolid, purified *E. coli* or *S. aureus* elongation factor P and the compound to be tested. The reaction is incubated at room temperature for 30 min. The reaction mixture is then carefully deposited in the center of the membrane disk on a vacuum manifold with very low vacuum setting and washed with 5 ml TKM buffer. The amount of membrane-bound EFP thus collected is measured by liquid scintillation spectrometry.

Efp function can be assayed as previously described M. C. Ganoza et al., *Eur. J. Biochem* 1985, vol. 146, pp. 287–294, and/or D-G. Chung et al. Chapter 4, pp. 69–80 of Ribosomes and Protein Synthesis, A Practical Approach, edited by G. Spedding, 1990, IRL Press at Oxford University Press, Oxford, N.Y. and Tokyo, both articles incorporated by reference.

Purification of Ribosomal Subunits without Efp

*S. aureus* cells (50 g wet weight) were resuspended in 100 ml of lysis buffer (50 mM Tris-HCl, pH 8.0, 100 mM NaCl, 2 mg/ml lysostaphin, 10,000 U Dnase I (Boehringer Mannheim, Indianapolis, Ind.)) and incubated for 1 h in a 37C water bath. Beta-mercaptoethanol was added to a final concentration of 5 mM, and the lysed cells were centrifuged at 10,000×g for 10 min to remove unbroken cells and cell fragments. The supernatant was centrifuged at 30,000×g and the resulting supernatant was centrifuged at 100,000×g for 16 h to pellet the ribosomes. The ribosome pellet was resuspended in Buffer B (20 mM Tris-HCl, pH 7.4, 1 M $NH_4Cl$, 5 mM $MgCl_2$, 1 mM DTT) and again centrifuged at 100,000×g for 16 h. The pellet was resuspended in Buffer A (60 mM $NH_4Cl$), applied to linear 5–40% (w/v) sucrose gradients prepared in Buffer A, and centrifuged for 16 h in a Beckman SW28 rotor. Gradients were fractionated, the 70S ribosomes were pooled, pelleted at 300,000×g for 5 h, and resuspended in Buffer A before storing at −80C.

One hundred grams of *E. coli* MRE600 grown in NS87 medium plus 1% yeast extract were washed with Buffer LM (10 MM Tris-HCl, pH 7.8, 10 mM $NH_4Cl$, 1 mM Mg(OAc)$_2$, 1 mM DTT), ground with two weights of alumina for 20 min and the paste extracted with 100 ml of Buffer LM containing 4 µg Dnase. An S30 fraction was prepared by centrifuging the suspension for 20 min at 20,000×g and recentrifuging the supernatant for 30 min at 30,000×g. The resulting supernatant fraction (S30) was adjusted to contain a final $NH_4Cl$ concentration of 1.0 M by slowly adding solid $NH_4Cl$. The salt-washed ribosomes were pelleted by centrifuging the S30 for 4 hr at 150,000×g. The washed ribosomes thus obtained were suspended in a small volume of Buffer LM and subjected to centrifugation in a 10–30% sucrose gradient in Buffer LM for 16 hr at 18,000 rpm in an SW28 rotor. The pooled fractions containing 30S and 50S subunits and the 70S tight couples were collected by pelleting at 100,000×g for 24 hr and resuspended in Buffer LM. The subunits were further purified by an additional round of sucrose gradient centrifugation. The purity of the subunits was verified by RNA analysis.

Purification of Ribosomal Subunits with Efp

*S. aureus* cells (50 g wet weight) were resuspended in 100 ml of lysis buffer (50 mM Tris-HCl, pH 8.0, 100 mM NaCl, 2 mg/ml lysostaphin, 10,000 U Dnase I (Boehringer Mannheim, Indianapolis, Ind.)) and incubated for 1 h in a 37C water bath. Betamercaptoethanol was added to a final concentration of 5 mM, and the lysed cells were centrifuged at 10,000×g for 10 min to remove unbroken cells and cell fragments. The supernatant was centrifuged at 30,000×g and the resulting supernatant was centrifuged at 100,000×g for 16 h to pellet the ribosomes. The ribosome pellet was resuspended in Buffer A (60 mM NH₄Cl) and again centrifuged at 100,000×g for 16 h. The pellet was resuspended in Buffer A, applied to linear 5–40% (w/v) sucrose gradients prepared in Buffer A, and centrifuged for 16 h in a Beckman SW28 rotor. Gradients were fractionated, the 70S ribosomes were pooled, pelleted at 300,000×g for 5 h, and resuspended in Buffer A before storing at −80C.

One hundred grams of *E. coli* MRE600 grown in NS87 medium plus 1% yeast extract were washed with Buffer LM (10 mM Tris-HCl, pH 7.8, 10 mM NH₄Cl, 1 mM Mg(OAc)₂, 1 mM DTT), ground with two weights of alumina for 20 min and the paste extracted with 100 ml of Buffer LM containing 4 μg Dnase. An S30 fraction was prepared by centrifuging the suspension for 20 min at 20,000×g and recentrifuging the supernatant for 30 min at 30,000×g. The resulting supernatant fraction (S30) was centrifuged for 4 hr at 150,000×g. The pelleted ribosomes thus obtained were suspended in a small volume of Buffer LM and subjected to centrifugation in a 10–30% sucrose gradient in Buffer LM for 16 hr at 18,000 rpm in an SW28 rotor. The pooled fractions containing 30S and 50S subunits and the 70S tight couples were collected by pelleting at 100,000×g for 24 hr and resuspended in Buffer LM. The subunits were further purified by an additional round of sucrose gradient centrifugation. The purity of the subunits was verified by RNA analysis.

Example 2

Elongation Factor P (efp) Tryptophan Fluorescence

Fluorescence measurements are carried out suing an ISS Spectroflurometer. The sample holder in the instrument is maintained at 26C using recirculated water from a constant temperature bath. Buffer solution consisting of 10 mM Tris-HCl pH 7.6, 10 mM MgCl₂, 50 mM NaCl, and 0.0001–0/001% Tween-20 is prepared. Other buffer systems such as HEPES, MOPS, Na-acetate, Na-phosphate may be used instead of Tris-HCl. The addition of Tween-20 or other nonionic detergent is necessary to prevent absorption of EFP to the walls of quartz cuvette. The buffer is passed through a 0.2 μm filter and degassed before use. Two milliliters of buffer are pipeted into a quartz cuvette (1 cm pathlength) containing a Teflon stir-bar. The quartz cuvette is placed into the temperature controlled sample holder of the spectrofluorometer. A solution of EFP protein (600 nM to 2.4 μM final protein concentration) is prepared by adding a specific volume of a stock solution of EFP protein to the cuvette containing 2 ml of buffer. A typical experiment uses 600 nM EFP, but data may be obtained with higher concentrations of protein. The cuvette containing the EFP solution is allowed to equilibrate with stirring for 10–15 minutes at 26C in the fluorometer. This time is required for equilibrium to occur between protein in solution and protein bound to the cuvette, and for the protein solution to reach the controlled temperature. A baseline fluorescence reading of EFP is obtained before adding any drug. The fluorescence of the single tryptophan residue (*S. Aureus* EFP) or three tryptophan residues (*E. Coli* EFP) are measured using an excitation wavelength of 295 nm and an emission wavelength of 330 nm. Slit widths for excitation and emission wavelengths are 1 mm. Excitation wavelengths between 270–300 nm, emission wavelengths between 310–350 mm, and other slit widths may be used to measure the tryptophan fluorescence of EFP protein. A stock solution of drug (oxazolidinone or other test substance) is prepared in 100% DMSO. A typical experiment uses a 2 mM solution of drug in 100% DMSO.

The drug is added in small increments (0.5–5.0 μl) and the fluorescence intensity at 330 nm is recorded after each addition. The final concentration of drug (oxazolidinone) is calculated after each drug addition. In a typical experiment, a total volume of 42 μl of 2 mM drug solution is added to give a final concentration of 42 μMolar oxazolidinone. The intensity of the tryptophan fluorescence is plotted vs drug concentration and the data is fit the following equation:

$$F = \left[\frac{(F_0 - (F_0 - F_{00})) \times I}{I + K_d}\right]^{-iXl}$$

where F is fluorescence intensity at 330 nm, $F_0$ is initial fluorescence without drug, $F_{00}$ is the fluorescence intensity where the protein is saturated with drug, I is the drug concentration, $K_d$ is the dissociation constant for the drug-protein interaction, and I is the correction factor for the inner filter effect. The oxazolidinones exhibit significant absorbance at the excitation wavelength (295 nm) so a correction for the inner filter effect of the drug is necessary. Goodness of fit of the experimental data tot he theoretical curve is evaluated using the residual sum of squares.

Example 3

Screening Assay

Radio-labeled compounds: [$^{14}$C]eperezolid (59.32 μCi/mg, 23.4 mCi/mmol), [$^{14}$C]linezolid (63.9 μCi/mg), and [$^3$H]eperezolid were synthesized at Pharmacia and Upjohn, Inc using standard technology. The binding studies were performed in microcentrifuge tubes that contained a total of 100 μl of reaction mixture which included 4–28 $A_{260}$ units of ribosomes containing efp, 1 to 100 μM of radio-labeled compound with either 1 μl of DMSO or an excess amount (100- to 1000-fold) of unlabeled compound, 50 mM Tris-HCl, pH 7.5, 5 mM Mg(OAc)₂, 200 mM KCl. All other ingredients were mixed together before the addition of ribosome. Ribosomes containing efp were prepared as described above. Alternately, ribosomes without efp can be prepared as described above and purified efp can be added. The reaction mixture was allowed to incubate at 25C for 10 min and was terminated by the addition of 50 μl ice-cold ethanol. After incubation at 4C for 30–60 min, the suspension was centrifuged at full speed in an Eppendorf for 20 min. The supernatant was then carefully removed and the radioactivity in the pellet measured. Nonspecific binding is defined as the number of dpm in the presence of an excess amount of unlabeled compound. The specific binding is determined by subtracting the nonspecific from the total binding.

Once the compounds that bind to either the 50S or 70S bacterial ribosomes have been identified, they will be screened for their ability to inhibit the formation of the translation initiation complex in the translation initiation complex assay.

The identification of compounds that compete with the binding of radiolabeled oxazolidinones to 50S or 70S bacterial ribosomes and inhibit the formation of the translation initiation complex.

Example 4

Initiation Complex Assay

*S. aureus* or *E. coli* 70S ribosomes, without efp, (10 pmol) were incubated with 9 pmoles [$^3$H]fmet-tRNA in duplicate 100 μl reactions containing 10 mM Tris-HCl, pH 7.4, 10 mM MgCl$_2$, 30 mM NH$_4$Cl, 1 mM DTT, various concentrations of the test compound and 100 pmol of the oligoribonucleotide (5'-rGGGAAUUCGGAGGUUUAAAAAUGGGUAAA-3'; SEQ ID NO:3). Duplicate reactions were incubated at 37C for 10 min and stopped by the addition of 2 ml of cold Buffer A (10 mM Tris-HCl, pH 7.4, 30 mM NH$_4$Cl, 10 mM MgCl$_2$, 1 mM DTT). Complexes were filtered through Millipore filters (0.45μ), washed with 50 μl of Buffer A and were counted after the addition of scintillation fluid. Compounds that inhibit the formation of the initiation complex would result in a decrease in the amount of [$^3$H]fmet-tRNA bound to the complex and trapped on the filter. A similar assay can be employed using 70S ribosomes in the presence of efp by purifying the ribosome subunits and efp as described above.

Example 5

Efp-Mediated First Peptide Bond Assay

Native efp purified from bacteria by the method of Aoki et al. is assayed in a total volume of 50 μl containing 1 ng - 1 mg of efp, 50 pmoles 70S ribosomes, 150 pmoles AUG or mRNA containing AUG, 5 pmoles radiolabeled Met-tRNA, 55 mM NH$_4$Cl, 8 mM MgCl$_2$, and 20 mM Tris-HCl, pH 7.4. The ribosomes are incubated for 5 min at 30C, and the AUG and radiolabeled fMet-tRNA are added. After a 30 min incubation at 30C, the efp source and puromycin (or suitable tRNA) are preincubated with each other for 1 min at 30C. The reaction is started by mixing the efp/puromycin solution with the ribosome/AUG/fMet-tRNA solution, followed by a min incubation at 30C. The reaction is stopped by adding 100 μl of 1 M potassium phosphate buffer, pH 6.0. The f-met-puromycin (or fmet-amino acid) is extracted with 1 ml of ethyl acetate, added to the scintillation cocktail, and counted in a scintillation counter.

Some of the preferred embodiments of the invention described above are outlined below and include, but are not limited to, the following claimed embodiments. As those skilled in the art will appreciate, numerous changes and modifications may be made to the preferred embodiments of the invention without departing from the spirit of the invention. It is intended that all such variations fall within the scope of the invention.

What is claimed is:

1. A method for identifying a compound which inhibits the first peptide bond reaction of a complex formed through the interaction of elongation factor p (efp), N-formylmethionyl-tRNA (fMet-tRNA), 30S subunit, 50S subunit, an mRNA containing an AUG sequence, initiation factors 1, 2, and 3, and a peptide bond donor comprising the steps of:
   (a) contacting efp with a first composition comprising fMet-tRNA, 30S subunit, 50S subunit, an mRNA containing an AUG sequence, initiation factors 1, 2, and 3, and a peptide bond donor to form a second composition;
   (b) contacting said second composition with a compound; and
   (c) determining whether said compound inhibits the first peptide bond reaction of the complex of fMet-tRNA, 30S subunit, 50S subunit, an mRNA containing an AUG sequence, initiation factors 1, 2, and 3, peptide bond donor, and efp.

2. The method of claim 1 wherein said peptide bond donor is either puromycin or a puromycin analog.

3. The method of claim 2 wherein said mRNA sequence is rArUrG.

4. The method of claim 1 wherein said peptide bond donor is an amino acyl-tRNA or an analog of amino acyl-tRNA.

5. The method of claim 4 wherein said mRNA sequence is rArUrG.

6. The method of claim 1 wherein said efp is isolated from a natural source.

7. The method of claim 6 wherein said natural source is a prokaryotic organism.

8. The method of claim 7 wherein said prokaryotic organism is bacteria.

9. The method of claim 8 wherein said bacteria is selected from the group consisting of *E. coli, S. aureus, S. pneumoniae, H. influenzae*, and an Enterococcus species.

* * * * *